(12) United States Patent
Rapp et al.

(10) Patent No.: US 9,888,833 B2
(45) Date of Patent: Feb. 13, 2018

(54) ENDOSCOPE WITH A RIGID CURVED SHAFT AS WELL AS PROCESS FOR PRODUCING SUCH AN ENDOSCOPE

(71) Applicant: Henke-Sass, Wolf GmbH, Tuttlingen (DE)

(72) Inventors: Stefan Rapp, Villingen-Schwenningen (DE); Norbert Haeckl, Leibertingen (DE)

(73) Assignee: Henke-Sass, Wolf GmbH, Tuttlingen (DE)

( * ) Notice: Subject to any disclaimer, the term of this patent is extended or adjusted under 35 U.S.C. 154(b) by 407 days.

(21) Appl. No.: 14/256,690

(22) Filed: Apr. 18, 2014

(65) Prior Publication Data

US 2014/0316194 A1 Oct. 23, 2014

(30) Foreign Application Priority Data

Apr. 19, 2013 (DE) .................... 10 2013 207 109

(51) Int. Cl.
*A61B 1/00* (2006.01)
*A61B 1/018* (2006.01)
(Continued)

(52) U.S. Cl.
CPC ........ *A61B 1/00078* (2013.01); *A61B 1/0011* (2013.01); *A61B 1/00071* (2013.01);
(Continued)

(58) Field of Classification Search
USPC .................. 600/121–125, 138, 151
See application file for complete search history.

(56) References Cited

U.S. PATENT DOCUMENTS 3,297,022 A * 1/1967 Wallace ............. A61B 1/00195
356/241.5
3,677,262 A * 7/1972 Zukowski .......... A61B 1/00165
385/117

(Continued)

FOREIGN PATENT DOCUMENTS

DE 202005017499 U1 1/2006
GB 1078036 8/1967
JP 09201325 5/1997

OTHER PUBLICATIONS

Extended European Search Report to the co-pending European patent application rendered by the European Patent Office (EPO) dated Aug. 27, 2016, 6 pages (including English translation).

*Primary Examiner* — Matthew J Kasztejna
(74) *Attorney, Agent, or Firm* — Skaar Ulbrich Macari, P.A.

(57) ABSTRACT

An endoscope is provided, with a main body and a rigid shaft, extending from the main body, which has a first section which extends in a rectilinear manner, a curved second section adjoining it and a third section, adjoining the second section, which forms a distal end of the shaft. The shaft includes, for receiving an instrument, a one-piece instrument tube which extends to the distal end of the shaft and has an open end there, and an optics module by means of which an image of an area in front of the distal end of the shaft can be recorded. A cladding tube extending from the main body to the distal end is provided, in which the instrument tube and the optics module are arranged, and which includes a rectilinear part for the first section and a curved part, connected to the rectilinear part, for the second section.

18 Claims, 3 Drawing Sheets

(51) Int. Cl.
   *A61B 1/12* (2006.01)
   *G02B 23/24* (2006.01)
   *A61B 1/05* (2006.01)
   *A61B 1/07* (2006.01)
   *A61B 1/06* (2006.01)

(52) U.S. Cl.
   CPC ............... *A61B 1/018* (2013.01); *A61B 1/05* (2013.01); *A61B 1/07* (2013.01); *A61B 1/128* (2013.01); *G02B 23/2476* (2013.01); *A61B 1/0684* (2013.01); *Y10T 29/49826* (2015.01)

(56) References Cited

U.S. PATENT DOCUMENTS

| | | | |
|---|---|---|---|
| 4,606,330 A | 8/1986 | Bonnet | |
| 4,646,722 A * | 3/1987 | Silverstein | A61B 1/00073 600/104 |
| 4,690,175 A * | 9/1987 | Ouchi | A61B 1/0055 138/131 |
| 5,083,549 A * | 1/1992 | Cho | A61B 1/00071 600/108 |
| 5,127,393 A * | 7/1992 | McFarlin | A61B 1/00154 600/114 |
| 5,199,417 A * | 4/1993 | Muller | A61B 1/07 600/128 |
| 5,363,882 A * | 11/1994 | Chikama | A61B 1/0055 138/103 |
| 5,463,712 A * | 10/1995 | Cawood | A61B 1/00181 385/117 |
| 5,647,840 A * | 7/1997 | D'Amelio | A61B 1/00091 600/169 |
| 5,735,792 A * | 4/1998 | Vanden Hoek | A61B 1/00087 600/138 |
| 5,876,330 A * | 3/1999 | Grabover | A61B 1/0011 600/129 |
| 6,143,013 A * | 11/2000 | Samson | A61M 25/005 604/264 |
| 6,165,123 A * | 12/2000 | Thompson | A61B 1/00078 600/114 |
| 6,761,684 B1 * | 7/2004 | Speier | A61B 1/00142 600/121 |
| 6,780,151 B2 * | 8/2004 | Grabover | A61B 1/00071 600/141 |
| 7,214,183 B2 * | 5/2007 | Miyake | A61B 1/00039 600/104 |
| 8,038,602 B2 * | 10/2011 | Gill | A61B 1/00059 600/121 |
| 8,075,478 B2 * | 12/2011 | Campos | A61B 1/0008 600/111 |
| 8,152,715 B2 * | 4/2012 | Root | A61B 1/00034 600/131 |
| 8,231,524 B2 * | 7/2012 | Schwartz | A61B 1/267 600/120 |
| 8,317,683 B2 * | 11/2012 | Efinger | A61B 1/00071 600/128 |
| 2005/0192477 A1 * | 9/2005 | Forster | A61B 1/0011 600/133 |
| 2006/0129030 A1 | 6/2006 | Dehmel | |
| 2008/0200761 A1 * | 8/2008 | Schwartz | A61B 1/267 600/120 |
| 2008/0269556 A1 * | 10/2008 | Jagasia | A61B 1/00098 600/104 |
| 2008/0293999 A1 * | 11/2008 | Halahmi | A61B 1/00071 600/101 |
| 2008/0300462 A1 * | 12/2008 | Intoccia | A61B 1/00071 600/146 |
| 2008/0308098 A1 * | 12/2008 | Schwartz | A61M 16/0488 128/200.26 |
| 2009/0018397 A1 | 1/2009 | Scholly et al. | |
| 2009/0281386 A1 * | 11/2009 | Acosta | A61B 17/3421 600/114 |
| 2010/0094090 A1 * | 4/2010 | Mejia | A61B 1/00052 600/120 |
| 2010/0298643 A1 | 11/2010 | Eisele | |
| 2013/0046139 A1 | 2/2013 | Daily et al. | |
| 2013/0204085 A1 * | 8/2013 | Alexander | A61B 1/05 600/109 |
| 2014/0187860 A1 * | 7/2014 | Yang | A61B 1/00071 600/114 |
| 2014/0213848 A1 * | 7/2014 | Moskowitz | A61B 1/00133 600/106 |
| 2014/0235940 A1 * | 8/2014 | Wang | A61B 1/00048 600/103 |
| 2016/0007834 A1 * | 1/2016 | Schoeler | A61B 1/0011 600/138 |

* cited by examiner

ENDOSCOPE WITH A RIGID CURVED SHAFT AS WELL AS PROCESS FOR PRODUCING SUCH AN ENDOSCOPE

PRIORITY

This application claims priority to German Patent Application No. 102013207109.4, filed on Apr. 19, 2013, which is hereby incorporated herein by reference in its entirety.

FIELD

The present invention relates to an endoscope with a rigid curved shaft as well as a process for producing such an endoscope.

BACKGROUND

Endoscopes are used for example in the medical field, e.g. for carrying out examinations and optionally treatments in the area of the nose. For this purpose, as a rule, such endoscopes have a curved instrument tube with an open distal end and a correspondingly curved optics tube. An image of the corresponding area in front of the distal end is recorded via the optics tube and an instrument can be positioned at the corresponding point via the instrument tube, for example to remove tissue. The optics tube and the instrument tube are connected to one another and can have several parts, with the result that the rigid shaft formed by the two tubes does not have a smooth outer surface but has recesses and edges. This is disadvantageous as dirt can collect there, with the result that it is difficult to clean and sterilize the endoscope.

SUMMARY

An object of certain embodiments of the invention is to provide an endoscope, with a rigid curved shaft, which has an instrument tube for receiving an instrument as well as an optics module for recording an image of an area in front of the distal end of the shaft and which can be easily cleaned.

According to certain embodiments, the object is achieved by an endoscope including a main body and a rigid shaft, extending from the main body, which includes a first section which extends in a rectilinear manner, a curved second section adjoining it and a third section, adjoining the second section, which forms a distal end of the shaft, wherein the shaft includes, for receiving an instrument, a one-piece instrument tube which extends to the distal end of the shaft and has an open end there, and an optics module by means of which an image of an area in front of the distal end of the shaft can be recorded, and wherein a cladding tube extending from the main body to the distal end is provided, in which the instrument tube and the optics module are arranged and which has a rectilinear part for the first section and a curved part, connected to the rectilinear part, for the second section.

The cladding tube can provide the shaft with a smooth outer surface on which on the one hand dirt cannot collect and which on the other hand is easy to clean. Since the cladding tube is formed of several parts, the endoscope according to certain embodiments is also easy to produce. In particular, the already curved instrument tube can be inserted with its curved section into the curved part and a rectilinear section of the instrument tube can be inserted into the rectilinear part. The two parts can then be connected to one another, resulting in the desired cladding tube.

The instrument tube in one preferred embodiment does not protrude out of the distal end of the cladding tube. In particular the distal end of the instrument tube can be flush with the distal end of the cladding tube.

The optics module can be inside the cladding tube and preferably does not protrude beyond the distal end.

The end of the curved part which faces away from the rectilinear part can form the distal end of the shaft. Alternatively it is possible for the cladding tube to have a third part which forms the distal end of the shaft and is connected to the curved part. The third part can in particular be produced from a solid material by machining, whereas the first and second parts can preferably be produced from a hollow tube, in particular an extruded hollow tube. The parts forming the cladding tube are preferably produced from stainless steel.

The parts which are connected to one another can be welded to one another. The weld points are preferably ground subsequently, with the result that the cladding tube has a smooth continuous outer surface.

The third part can be formed in one piece and have an end plate which seals the end facing away from the curved part, wherein an opening for the instrument tube and at least one opening for the optics module are provided in the end plate.

The at least one opening for the optics module in the end plate can be sealed by means of a transparent disc or plate. In particular it can be a glass sheet or glass disc (for example sapphire glass). The glass can be soldered to seal the opening hermetically.

The curved part can have a curvature of greater than 0° and smaller than 120°, in particular a curvature of greater than or equal to 10° and smaller than or equal to 110°. Furthermore, the curvature can lie in the range of from 10° to 100°, 10° to 90°, 20° to 120°, 30° to 120° or 45° to 120°.

The optics module can in particular embodiments be arranged at the distal end in the shaft. The optics module can have at least one imaging lens system (e.g. objective lens). Furthermore, the optics module can have an image sensor, such as e.g. a CMOS or CCD sensor, arranged directly behind the imaging lens system. Alternatively a transmission lens system, which transmits the recorded image into the main body, can be arranged downstream of the imaging lens system. An image sensor can be arranged in the main body to record the transmitted image. Alternatively or in addition an optical view device can be provided on the main body via which a user can see the image transmitted into the main body.

Furthermore, the endoscope according to certain embodiments of the invention can include an illumination system which illuminates the recordable area via the distal end. The illumination system can for example have a light source at the distal end. Alternatively, the light source can be arranged in the main body. To transmit the light of the light source for example an optical fibre can be used which then runs from the main part via the shaft to the distal end. The light source can in particular be a light-emitting diode or a laser diode. The light source preferably emits light in the visible spectral range. Alternatively or in addition it can also emit light in other wavelength ranges such as e.g. in the infrared range.

It is possible for the endoscope itself not to have a light source, but to have only an optical fibre connection on the main body via which light from an external light source can then be guided to the distal end.

The instrument tube in certain preferred embodiments has a cross-section shape which comprises, in addition to an area with a circular cross-section, also a further area. This further area can then, with an inserted instrument which occupies the area with the circular cross-section, be used as an irrigation and/or suction channel. In particular, the instrument tube can have a D-shaped cross-section.

The cladding tube can include an elongated cross-section shape which has two rounded ends lying opposite one another as well as two sides which connect the ends and extend in a rectilinear manner. The rounded ends can in particular have a curve with a constant radius and in particular a semi-circular curve. The sides which extend in a rectilinear manner can in particular be parallel to one another.

As already stated, it is possible to arrange in the main body a light source, the light of which is guided via an optical fibre system to the distal end to illuminate the recordable area in front of the distal end.

The light source can be in direct mechanical contact with a first heat-conducting body which conducts heat generated by the light source to a housing wall of the main body, wherein the thermal conductivity of the first heat-conducting body is greater than that of the housing wall. Thus the housing wall can be produced for example from stainless steel and the first heat-conducting body can be produced from aluminum.

In the endoscope according to certain embodiments of the invention it is possible to arrange in the main body at least one further heat-conducting body which is in thermal contact with the first heat-conducting body and is loaded with a force which pushes it against the inside of the housing wall. In particular, two further heat-conducting bodies can be arranged which lie opposite one another. The two heat-conducting bodies can be pushed away from one another. For this purpose a screw can be used, for example, which is guided into an internal thread at least in one of the two heat-conducting bodies. The end of the screw which faces away from the internal thread can push against the other heat-conducting body. By setting the screw appropriately the two heat-conducting bodies can be pushed away from one another.

In the endoscope according to certain embodiments of the invention the thermal contacting of the heat-conducting body with the housing wall can be generated purely by touch without thermal adhesive or thermal conducting paste. Alternatively it is possible to use a thermal adhesive or a thermal conducting paste.

In the endoscope according to certain embodiments of the invention the main body and the shaft except for the instrument tube can be hermetically sealed with respect to the surroundings and can thus be autoclavable. Here, by autoclavable is meant in particular that the endoscope is exposed, for a specified period (for example several minutes), to water vapor (in particular saturated water vapor) of from at least 100° C. or at least 130° C. for sterilization, without the endoscope being damaged (in particular without water vapor being able to penetrate the shaft (except for the instrument tube) and the main body).

The object can be furthermore achieved in certain embodiments by a process for producing an endoscope according to the invention in which the following steps are carried out:
a) inserting a curved section of the instrument tube into the curved part,
b) inserting a rectilinear section of the instrument tube into the rectilinear part, and
c) (permanently) connecting the two parts.
Steps a) and b) can be carried out in any order. The connecting according to step c) can for example be carried out by welding.

The process according to certain embodiments of the invention can feature the step of bending the instrument tube. Furthermore it can feature the step of bending a rectilinear hollow tube to produce the curved part.

The process according to certain embodiments of the invention can include the process steps described in connection with the endoscope according to the invention including developments thereof. Furthermore it can include the process steps to produce the endoscope according to the invention including developments thereof.

It is understood that the features mentioned above and those yet to be explained below can be used, not only in the stated combinations, but also in other combinations or singly, without departure from the scope of the present invention.

BRIEF DESCRIPTION OF THE DRAWINGS

The invention is explained in further detail below by way of example with reference to the attached drawings which also disclose features essential to the invention. There are shown in.

DETAILED DESCRIPTION

The present invention can be explained with reference to the following example embodiments. However, these example embodiments are not intended to limit the present invention to any specific examples, embodiments, environments, applications or implementations described in these embodiments. Therefore, description of these embodiments is only for purpose of illustration rather than to limit the present invention.

Figure 1:
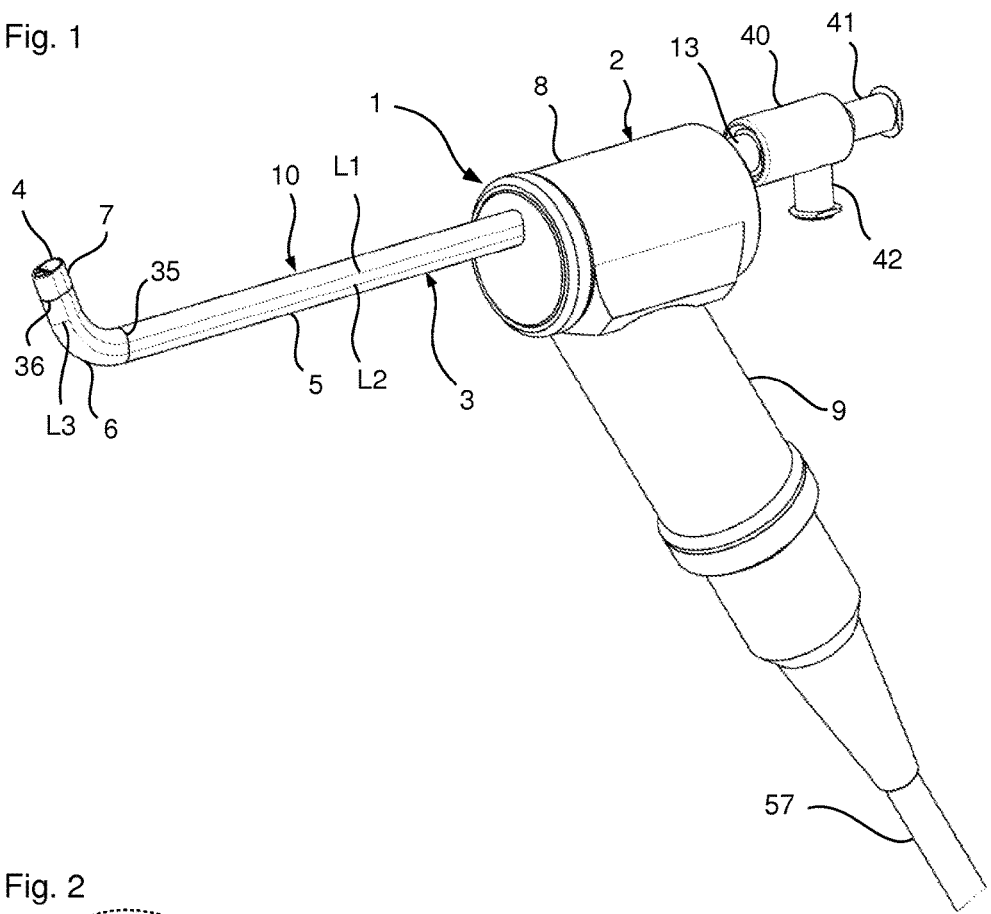
FIG. 1 is a perspective view of an embodiment of the endoscope according to certain example embodiments.

Referring to FIG. 1, the endoscope 1 comprises a main body 2 and a rigid shaft 3 connected to it, which is bent at the distal end 4 facing away from the main body 2. Because of the rigid formation of the shaft, this bending cannot be changed.

The rigid shaft 3 includes a first rectilinear section 5, connected to the main body 2, which is adjoined by a second curved section 6. A third section 7 which forms the distal end 4 of the shaft 3 adjoins the second section 6.

The main body 3 includes a main part 8, to which the shaft 3 is connected, as well as a handle 9.

Figure 2:
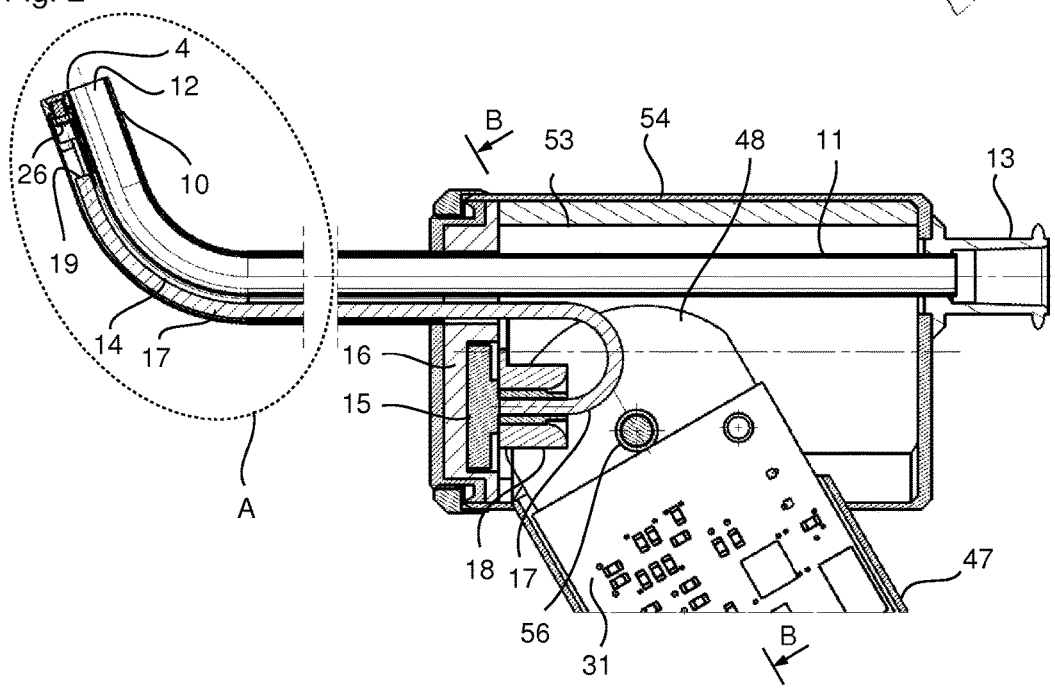
FIG. 2 is a sectional view of the endoscope according to FIG. 1.

As can be seen most clearly from the sectional representation according to FIG. 2, the shaft 3 comprises a cladding tube 10, which extends from the distal end 4 into the main part 8. In the cladding tube 10 an instrument tube 11 is arranged which extends to the distal end 4 and has an open end 12 there. Although the distal end of the cladding tube 10 is sealed with an end plate 60 (FIG. 3), the end plate 60 has an opening 61 for the instrument tube 11, with the result that the open end 12 is accessible from the outside. The instrument tube 11, which is formed in one piece and thus has no interruptions, extends from the distal end 4 through the main part 8 of the main body 2 and opens in a connecting sleeve 13. An instrument can be inserted into the instrument tube 11 via the connecting sleeve 13 and pushed to the distal end 4 and beyond, as the instrument tube 11 has the open end 12 at the distal end 4.

In addition, provided in the cladding tube 10 there is an optics channel 14 which, as is described in detail below, serves to be able to illuminate an area in front of the distal end 4 and record an image of the illuminated area.

To illuminate the area in front of the distal end 4, in the main part 8 in a baseplate 16 made of aluminum a light-emitting diode 15 is positioned which emits illumination light which is coupled into an optical fibre 17 positioned in front of the light-emitting diode 15. For this purpose one end of the optical fibre 17 is positioned directly in front of the light-emitting diode 15 via a holder 18.

The optical fibre 17 extends from the light-emitting diode 15 through the inside of the main part 8 into the optics channel 14 of the cladding tube 10 and runs inside this to the distal end 4. As the end plate 60 has two illumination openings 20, 21, as can be seen most clearly in FIG. 3 in which a top view of the distal end 4 is shown, after passing through the second curved section 6 of the shaft 3 the optical fibre 17 divides at a branching point 19 into two optical fibre sections which run to the two illumination openings 20, 21. In the representation according to FIG. 2 the two optical fibre sections therefore run towards the front and towards the back out of the plane of drawing according to FIG. 2. In the sectional representation according to FIG. 2 the optical fibre 17 therefore seems to end at the branching point 19.

Figure 3:
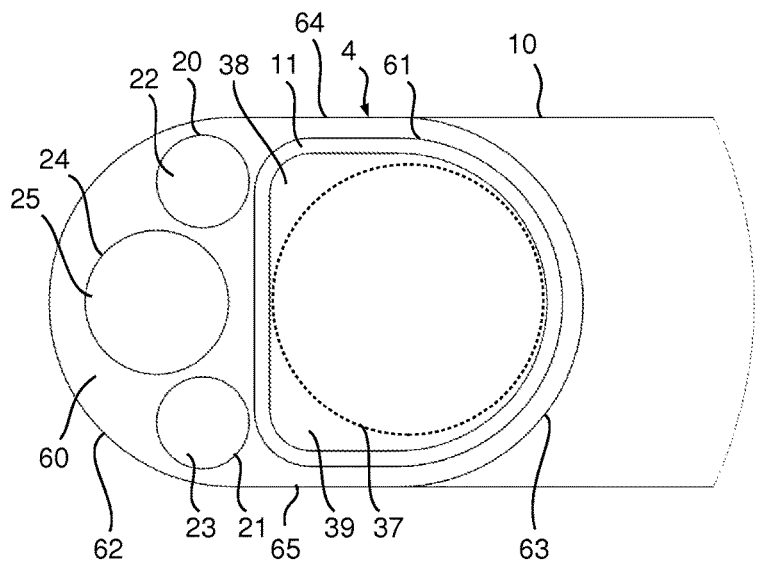
FIG. 3 is an enlarged top view of the distal end of the shaft of the endoscope according to FIGS. 1 and 2.

The two illumination openings 20, 21 are each hermetically sealed with a cover glass 22, 23 (FIG. 3). In the end plate 60 in the distal end 4 between the two illumination openings 20 and 21 a further opening 24 is formed, which is again hermetically sealed with a cover glass 25. The recording of the image of the illuminated area in front of the distal end 4 takes place via this opening 24. For this purpose a recording module 26 is arranged behind the cover glass 25 in the optics channel 14. This can be seen particularly well in the sectional representation of FIG. 4 in which detail A from FIG. 2 is represented enlarged.

The recording module 26 comprises, behind the cover glass 25, an objective lens 27 and an image sensor 28 (which is here formed as a CMOS sensor) which sit in a holder 29 which serves to position the objective lens 27 and the image sensor 28 behind the cover glass 25. Furthermore a cable 24 (here ribbon cable) is also represented schematically in FIG. 4 which is connected to the image sensor 28 and runs from the image sensor 28 via the optics channel 14 to a corresponding electronic control unit, of which one of two circuit boards 31 is drawn schematically in FIG. 2, in the handle 9. To simplify the representation the cable 30 shown ends before the curved second section 6.

The cladding tube 10 is formed here of three parts 32, 33 and 34 which are welded to one another at the points 35 and 36. The first part 32 forms the straight section 5. The second part 35 forms the curved second section 6 and the third part 34, together with the second part 33, forms the third section 7 of the shaft 3. The second part 35 can have an area at each of its two ends which extends in a straight line and then forms part of the first or third section 5, 7. The curved second part 33 is here curved such that an angle α between the longitudinal direction of the third section 7 and the longitudinal direction of the first section 5 is 70°. The angle α is preferably greater than 0° and smaller than or equal to 120°. In particular, the angle α is greater than or equal to 10° and smaller than or equal to 110°.

This formation of the cladding tube 10 in several parts allows the endoscope 1 according to the invention or the shaft 3 of the endoscope 1 according to the invention to be easy to produce. Thus, to produce the endoscope 1 the one-piece instrument tube 11 with its distal end is pushed through the curved second part 33 until the curved section of the instrument tube 11 rests against the correspondingly curved second part 33 on the inside. Then the third part 34 is pushed on from the distal end side and the first part 32 from the proximal end side. The first part 32 is then welded to the second part 33 at the point 35 and the third part 34 is welded to the second part 33 at the point 36.

Of course, the order in which the third and first parts 34, 32 are pushed on can also be reversed. Furthermore the welding can also be carried out at the point 36 first and then at the point 35. Finally, it is also possible to carry out the corresponding welding after pushing on the first or third part 32, 34, and then to push on and weld the remaining part (third or first part 34, 32).

Before the third part 34 is pushed onto the instrument tube 11, the recording module 26 as well as the ends of the optical fibre sections of the optical fibre 17 can be secured in the third part 34. Furthermore, the cover glasses 22, 23 and 25 can also already be inserted. The cover glasses 22, 23 and 25 are preferably soldered, with the result that they hermetically seal into the corresponding opening 20, 21, 24. Finally, the instrument tube 11 is also soldered or welded in the distal end to the corresponding opening 61 in the end plate 60, with the result that a hermetically sealed connection is also present here in such a way that fluid can indeed flow into the instrument tube 11 or out of the instrument tube 11 via the open end 12 of the instrument tube 11. However, there is no connection from the instrument tube 11 or the inside of the instrument tube 11 to the optics channel 14 or to the inside of the main body 2. Both the optics channel 14 and the main body 2 are thus hermetically sealed with respect to the surroundings.

As can be seen in particular from the representation in FIG. 3, the instrument tube 11 has a substantially D-shaped cross-section. It is thus advantageously achieved that when an instrument 37 is arranged in the instrument tube 11, as is indicated by the dashed circle in FIG. 3, in the instrument tube 11 there are still two free areas 38, 39 which can be used for rinsing and/or suction. A rinsing fluid can be fed, via these areas 38, 39, to the area in front of the distal end 4. Furthermore, corresponding material can be suctioned off via these areas 38, 39. As indicated in FIG. 1, for this purpose it is possible to provide on the connecting sleeve 13 a T-shaped connecting element 40 which provides a means of access 41 for the instrument to be inserted on the one hand and has a suction/irrigation connection 42 on the other hand. The connecting element 40 is drawn in only in FIG. 1 and not in FIG. 2. This rinsing facility makes it possible to remove e.g. dirt from in front of the cover glass 25, 22 and/or 23 while using the endoscope 1, with the result that permanently good recording conditions for the recording module 26 can be created and maintained.

The D-shaped cross-section of the instrument tube 11 leads to the already described advantage that with an inserted instrument 37 there are still free areas 38, 39 which can be used as irrigation and/or suction channel. Moreover, the D-shaped cross-section is extremely compact, with the result that the cross-section of the cladding tube 10 can also be kept as small as possible. In addition to the D-shaped cross-section of the instrument tube 11 other cross-section shapes are, of course, also possible, which are preferably selected such that in addition to a circular cross-section area (here for the instrument 37) there is still at least one free area (here areas 38 and 39) which can be used as irrigation and/or suction channel.

In order that the cladding tube 10 can receive the instrument tube 11 it does not have a circular cross-section but rather a cross-section which deviates from the circular and which can for example be called a double-D cross-section. The cross-section therefore has two curved (here semicircular) ends 62, 63 which are connected by rectilinear sides 64, 65 which e.g. run parallel to one another (FIG. 3). In order to be able to better represent this cross-section shape of the cladding tube 10 in the perspective view in FIG. 1, two auxiliary lines L1, L2, extending in the longitudinal direction of the cladding tube, are drawn in which illustrate the transition of the two ends 62, 63 to the rectilinear side 65. In addition, another auxiliary line L3 is drawn in which indicates the transition from the curved second section 6 to the third section 7 extending in a rectilinear manner.

Figure 5:
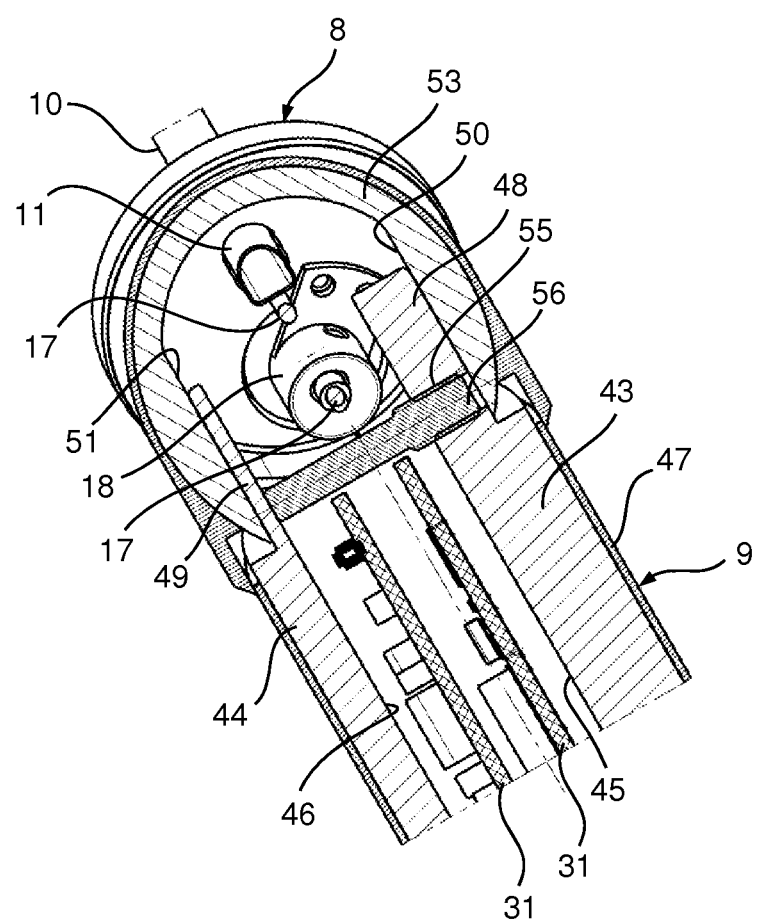
FIG. 5 is an enlarged sectional view along the section line B-B in FIG. 2.

The circuit boards 31 arranged in the handle 9 serve to control the image sensor 28 as well as the light-emitting diode 15. The circuit boards 31 are arranged in the handle 9 between a first and a second heat-conducting body 43 and 44. This can be seen in particular in FIG. 5 which shows a sectional representation along the section line B-B of FIG. 2. The heat-conducting bodies 43, 44 have flat insides 45, 46 facing towards one another. The outer sides of the two heat-conducting bodies 43 and 44 are adapted to the internal contour of the hollow cylinder-shaped wall section 47 of the handle 9. Both the first and the second heat-conducting bodies 43, 44 each have a protruding section 48, 49 which project into the main part 8 and rest in each case against the corresponding inside 50, 51 of a third heat-conducting body 53 which rests with its outer side against the substantially hollow cylinder-shaped wall section 54 of the main part 8. The third heat-conducting body 53 has a substantially U-shaped cross-section. The third heat-conducting body 53 is in contact with the base 16, as can be seen clearly in FIG. 2.

The protruding section 48 of the first heat-conducting body 43 has an internal thread 55 in which a screw 56 is screwed, the end of which facing away from the internal thread 55 pushes against the protruding section 49 of the second heat-conducting body 44. The screw 56 is screwed into the internal thread 55 such that the two protruding sections 48, 49 are pushed away from one another and thus against the insides 50, 51 of the third heat-conducting body 53. Thus a surface contact exists between the protruding sections 48 and 49 and the third heat-conducting body 53. This also leads to the third heat-conducting body 53 being pushed against the inside of the hollow cylinder-shaped wall section 54. Furthermore, the spreading of the two protruding sections 48, 49 by means of the screw 56 leads to the first and second heat-conducting bodies 43 and 44 resting well against the hollow cylinder-shaped wall section 47.

The heat-conducting bodies 43, 44 and 53 as well as the base 16 are produced from aluminum, have a high thermal conductivity or a higher thermal conductivity than the wall sections 47 and 54 and serve to convey the heat forming during the operation of the light-emitting diode 15 to the hollow cylinder-shaped wall sections 47 and 54 over a large surface area and thus to dissipate it towards the outside. The heat-conducting bodies 43, 44 and 54 thus serve to spread the heat. The hollow cylinder-shaped wall sections 47 and 54 are produced from stainless steel and have a significantly lower thermal conductivity than the heat-conducting bodies 43, 44 and 53. However, due to the contact over a large surface area, the heat dissipation can be ensured.

The contact between the individual heat-conducting bodies 43, 44 and 53 is ensured by the spreading of the two protruding sections 48 and 49 and the contact of the heat-conducting bodies 43, 44 and 53 with the corresponding wall sections 47 and 54 is ensured by the application of force, which is the result of the spreading. If necessary and/or desired, the heat-conducting bodies 43, 44 and 54 and the base 16 can be adhesively secured to one another and/or to the corresponding wall sections 47 and 54.

At the lower end of the handle 9 a cable 57 is also drawn in in FIG. 1 which serves on the one hand to supply power to the light-emitting diode 15, the circuit boards 31 and the image sensor 28. On the other hand, the image data of the images recorded by means of the image sensor 28 are delivered to the outside via the cable 57. For this purpose, for example, a connector (not shown) is provided at the end of the cable 57.

The entire endoscope 1, except for the instrument tube 11, is formed to be hermetically sealed with respect to the surroundings. In particular the optics channel 14 and the main body 2 are hermetically sealed with respect to the surroundings and the inside of the instrument tube 11. For this purpose the cladding tube 10 as well as the wall parts of the main body are here produced from stainless steel. The connection points to be sealed are preferably welded. Thus the endoscope 1 is autoclavable.

As the instrument tube 11 is formed in one piece and thus has no interruptions, the endoscope 1 can be cleaned and sterilized very well in an autoclave process.

The formation of the cladding tube 10 in several parts thus makes it possible to provide an endoscope, with a rigid shaft 3 the end of which is bent, in which the outer contour of the shaft 3 is smooth and has no edges, recesses, undercuts or projections on which dirt can easily collect. The weld points 35 and 36 can be ground down such that there is no bump but rather the cladding tube 10 has a smooth outer surface.

Figure 4:
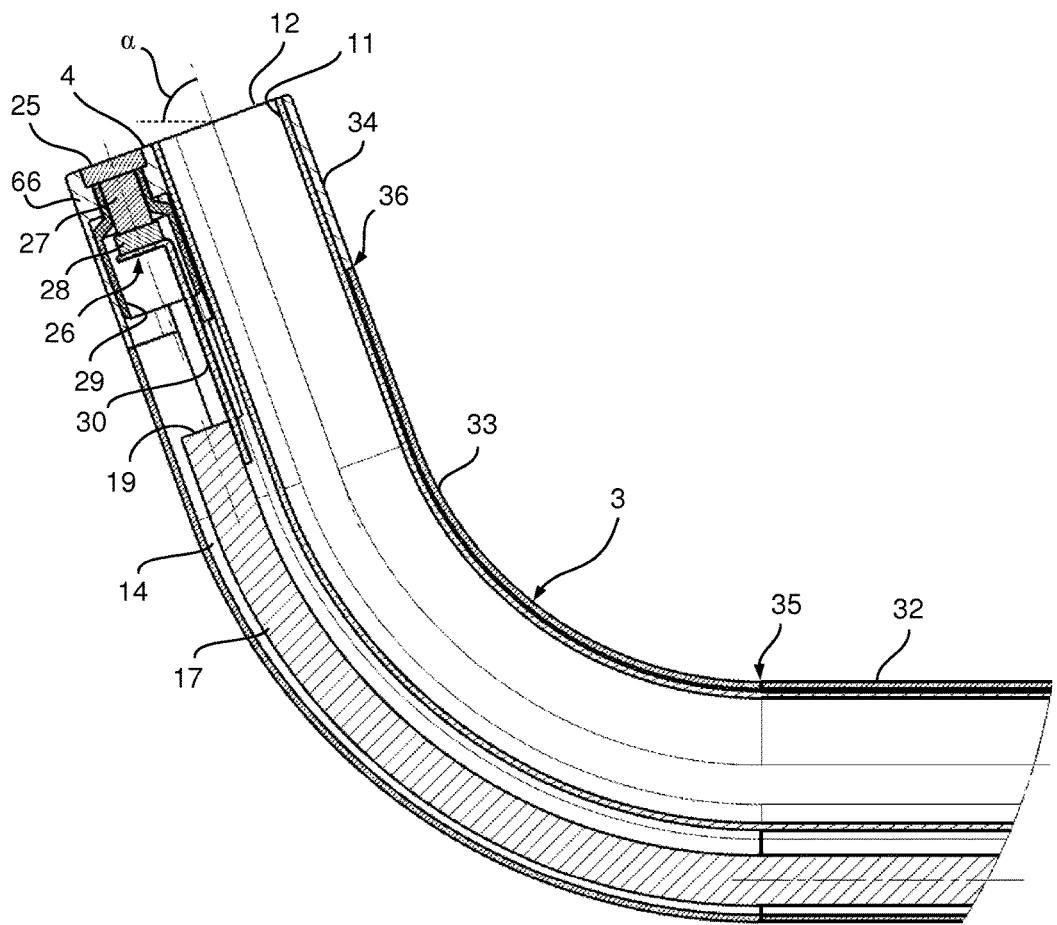
FIG. 4 is an enlarged view of detail A from FIG. 2.

The first and second parts 32 and 33 of the cladding tube are preferably produced from hollow tubing. This can in particular be tubing produced by drawing. Such tubing can be bent well. The third part 36 is preferably produced from a solid material by machining. The distal end 4 and in particular the end plate 60 with the openings 20, 21, 24 and 61 can thus be produced well. In particular, the openings 20, 21 and 24 can be produced such that the respective cover glass 22, 23 and 25 in the inserted state is flush with the upper side of the upper plate 60. In addition, a corresponding seat 66 can be formed for the optics module 26 (FIG. 4).

The endoscope 1 according to the invention is in particular formed as an endoscope for use in the medical field. Furthermore it can serve as an endoscope 1 for use in the ear, nose and throat field.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:
1. An endoscope, comprising:
   a main body;
   an optics module; and
   a rigid shaft, the rigid shaft extending from the main body, and including an instrument tube for receiving an instrument and a cladding tube in which the instrument tube and the optics module are disposed,
wherein the instrument tube is formed as one-piece and is rigid for its entire length, wherein the instrument tube extends to a distal end of the rigid shaft and includes an open end adjacent the distal end of the rigid shaft, and wherein the optics module is configured to record an image of an area in front of the distal end of the rigid shaft,
wherein the cladding tube comprises a first section which extends in
a rectilinear manner, a curved second section adjoining the first section, wherein each of the first section and second section of the rigid shaft are rigid and formed as separate sections, wherein the first and second sections of the cladding tube are joinable to span from the main body to the distal end, wherein the instrument tube is disposed within the joined first section and second section of the cladding tube, and wherein, when the first section and second section are joined, the cladding tube defines a stepless outer surface spanning from the main body to the distal end, and
wherein, when the first section and second section are joined, the cladding tube defines a constant outer diameter as the cladding tube spans from the main body to the distal end.

2. The endoscope according to claim 1, wherein the cladding tube includes a third section that is rigid, forms the distal end of the rigid shaft, and is formed as a separate section, wherein the third section is joined to the second section.

3. The endoscope according to claim 2, wherein the third section includes an end plate which seals the end facing away from the curved part, wherein an opening for the instrument tube and at least one opening for the optics module are formed in the end plate.

4. The endoscope according to claim 1, wherein the sections of the cladding tube which are connected to one another are welded to one another.

5. The endoscope according to claim 1, wherein the curved second section has a curvature of greater than 0° and smaller than 120°.

6. The endoscope according to claim 5, wherein the curved second section has a curvature of greater than or equal to 10° and smaller than or equal to 110°.

7. The endoscope according to claim 1, wherein the optics module includes an image sensor disposed adjacent the distal end.

8. The endoscope according to claim 1, wherein the instrument tube includes either a circular cross-sectional shape portion or a D-shaped cross-sectional shape portion.

9. The endoscope according to claim 1, wherein the cladding tube has an elongated cross-section shape, two rounded ends lying opposite one another, and two sides which connect the ends and extend in a rectilinear manner.

10. The endoscope according to claim 1, wherein in the main body a light source is disposed and arranged to emit light which is guided via an optical fibre system to the distal end to illuminate a recordable area adjacent the distal end.

11. The endoscope according to claim 1, wherein in the main body a light source is disposed in direct mechanical contact with a first heat-conducting body which conducts heat generated by the light source to a housing wall of the main body, wherein the thermal conductivity of the first heat-conducting body is greater than that of the housing wall.

12. The endoscope according to claim 11, wherein in the main body at least one further heat-conducting body is arranged which is in thermal contact with the first heat-conducting body and is loaded with a force which pushes it against the inside of the housing wall.

13. The endoscope according to claim 11, wherein the thermal contacting of the heat-conducting body with the housing wall is generated solely by touch and without either thermal adhesive or thermal conducting paste.

14. The endoscope according to claim 1, wherein the main body and the rigid shaft, except for the instrument tube, are hermetically sealed with respect to the surroundings and are autoclavable.

15. The endoscope according to claim 1, wherein the instrument tube extends from the main body to the distal end of the rigid shaft.

16. A process for producing an endoscope according to claim 1, comprising the steps of:
inserting a curved section of the instrument tube into the curved part;
inserting a rectilinear section of the instrument tube into the rectilinear part; and
connecting the curved part to the rectilinear part.

17. An endoscope, comprising:
a main body;
an optics module; and
a shaft, the shaft extending from the main body, and including an instrument tube for receiving an instrument and a cladding tube in which the instrument tube and the optics module are disposed,
wherein the instrument tube comprises a single piece and is rigid for its entire length, wherein the instrument tube extends to the distal end of the shaft and includes an open end adjacent the distal end of the shaft,
wherein the cladding tube comprises a first section which extends in a rectilinear manner, a curved second section joined to the first section, and a third section joined to the second section, wherein the third section forms a distal end of the shaft, wherein each of the first section, second section and third section are rigid and formed as separate sections, wherein the first, second, and third sections of the cladding tube are joinable to span from the main body to the distal end such that the cladding tube, when the first, second, and third sections are joined, defines a stepless outer surface, wherein the instrument tube is disposed within the joined first section, second section and third section, and
wherein when the cladding tube, when the first, second, and third sections are joined, the cladding tube defines a constant outer diameter as the cladding tube spans from the main body to the distal end.

18. The endoscope of claim 17, wherein the optics module is disposed in the shaft and positioned to record an image of an area in front of the distal end of the shaft.

* * * * *